(12) United States Patent
Iverson et al.

(10) Patent No.: US 7,186,376 B2
(45) Date of Patent: Mar. 6, 2007

(54) SLOW RELEASE PRODUCTION OF CHLORINE DIOXIDE FROM ACIDIFIED SODIUM CHLORITE

(76) Inventors: Carl E. Iverson, 507 Pear St. NE., Olympia, WA (US) 98506; Scott P. Ager, 301 Lee St. SW. Apt. 7, Tumwater, WA (US) 98501

( * ) Notice: Subject to any disclaimer, the term of this patent is extended or adjusted under 35 U.S.C. 154(b) by 640 days.

(21) Appl. No.: 10/094,016

(22) Filed: Mar. 7, 2002

(65) Prior Publication Data

US 2002/0136684 A1 Sep. 26, 2002

Related U.S. Application Data

(60) Provisional application No. 60/274,007, filed on Mar. 7, 2001.

(51) Int. Cl.
*A61L 2/00* (2006.01)
(52) U.S. Cl. .............................. 422/37; 422/28; 422/29; 426/332; 426/335
(58) Field of Classification Search ..................... 422/3, 422/9, 34, 256, 37, 28, 29; 426/332, 335
See application file for complete search history.

(56) References Cited

U.S. PATENT DOCUMENTS

| | | | | |
|---|---|---|---|---|
| 4,143,115 A | * | 3/1979 | Ward et al. ................. | 422/113 |
| 5,084,210 A | * | 1/1992 | Teeters ........................ | 252/392 |
| 5,389,390 A | * | 2/1995 | Kross ......................... | 426/332 |
| 6,120,731 A | * | 9/2000 | Kross et al. .................. | 422/29 |
| 6,325,970 B1 | * | 12/2001 | Parkinson et al. ............ | 422/29 |
| 2002/0014463 A1 | * | 2/2002 | Iverson et al. .............. | 210/749 |
| 2002/0061263 A1 | * | 5/2002 | Taylor ........................ | 422/129 |

* cited by examiner

*Primary Examiner*—Krisanne Jastrzab
(74) *Attorney, Agent, or Firm*—Delbert J Barnard

(57) ABSTRACT

A sodium chlorite ($NaClO_2$) solution is admixed with flowing water to form a flowing water and sodium chlorite ($NaClO_2$) solution. A flowing water and acid solution is admixed into the flowing water and sodium chlorite ($NaClO_2$) solution. The combined solutions are directed into and through a mixing chamber to form a homogenous, acidified sodium chlorite solution. The homogenous, acidified sodium chlorite solution is removed from the mixing chamber and is either utilized as a liquid or is frozen to form ice that is utilized. The acidified sodium chlorite solution provides a slow release of chlorine dioxide gas ($ClO_2$) for use in water treatment, in food plant sanitation, in ice for icing food items, and as an antimicrobial solution for direct application to food items.

17 Claims, 3 Drawing Sheets

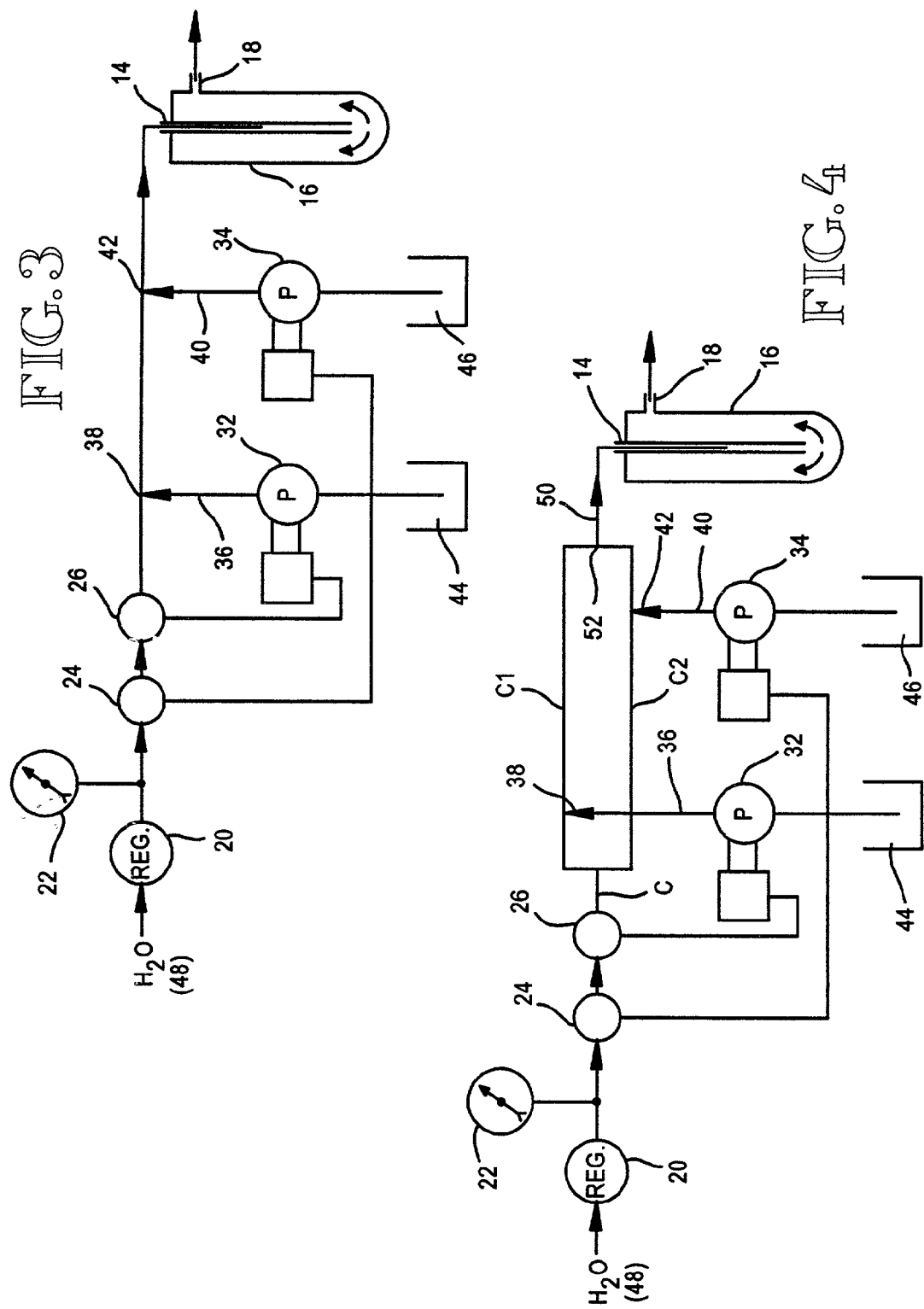

SLOW RELEASE PRODUCTION OF CHLORINE DIOXIDE FROM ACIDIFIED SODIUM CHLORITE

CROSS REFERENCE TO RELATED APPLICATION

This application claims benefit of the filing of U.S. provisional patent application Ser. No. 60/274,007, filed Mar. 7, 2001, and entitled, "Automatic Metering System For Acidified Sodium Chlorite."

TECHNICAL FIELD

This invention relates to a method and apparatus for producing acidified sodium chlorite solutions of predetermined concentrations and time released properties. The solution provides a slow release of chlorine dioxide for use in water treatment, in food plant sanitation, in ice for icing food items, and as an antimicrobial solution for direct treatment of food items.

BACKGROUND INFORMATION

It is known to mix sodium chlorite and mineral acid solutions together in a concentrated form. The mixing occurs within a few minutes and the object is to maximize the production of chlorine dioxide from the reactants. This concentrate is then diluted with water down to application levels of parts per million for use to eliminate spoilage and pathogenic organisms on food items. An object of the present invention is to provide a method and apparatus for deliberately mixing the sodium chlorite and acid solutions in a water stream in such a way that the chlorine dioxide forms slowly over a period of hours and even days.

Known systems for producing and/or using chlorine dioxide are disclosed in the following United States patents: U.S. Pat. No. 4,013,761, granted Mar. 22, 1977 to William J. Ward and Kenneth E. Gasper; U.S. Pat. No. 4,534,952, granted Aug. 13, 1985, to W. Howard Rapson and Maurice C. J. Fredette; U.S. Pat. No. 4,925,645, granted May 15, 1990, to James A. Mason; U.S. Pat. No. 5,009,875, granted Apr. 23, 1991, to Joseph M. Kelley, Donald C. Kucher and George Mayurnik; U.S. Pat. No. 5,618,440, granted Apr. 8, 1997, to James A. Mason; U.S. Pat. No. 5,799,833, granted Sep. 1, 1998, to Thomas S. Green and Eric G. Hilston; U.S. Pat. No. 5,863,584, granted Jan. 26, 1999, to Thomas Iverson Jr., Joyce Prindle and Robert E. Keith; U.S. Pat. No. 6,004,604, granted Dec. 21, 1999 to Thomas Iverson Jr., Joyce Prindle and Robert E. Keith; and U.S. Pat. No. 6,120,731, granted Sep. 19, 2000, to Robert D. Kross and Kere Kemp.

DISCLOSURE OF THE INVENTION

A principal object of the present invention is to produce a method that is basically characterized by admixing a flowing water and acid solution into a flowing water and sodium chlorite ($NaClO_2$) solution. The combined solutions are directed into and through a mixing chamber. In the mixing chamber, they are mixed to form a homogeneous, acidified sodium chlorite solution. According to an aspect of the invention, the homogenous, acidified sodium chlorite solution is removed from the mixing chamber and delivered to an environment in which chlorine dioxide ($ClO_2$) is desired. In that environment, the chlorine dioxide ($ClO_2$) is slowly produced by and released from the homogenous, acidified sodium chlorite solution over a period of time.

According to another aspect of the invention, the flowing water and acid solution are formed by admixing a flowing acid solution into a flowing water stream. Preferably, about one part acid solution is admixed with about one thousand eight hundred (1,800) parts of water. Preferably also, about one part sodium chlorite ($NaClO_2$) solution is admixed into about one thousand eight hundred (1,800) parts of water.

The homogenous, acidified sodium chlorite solution may be delivered from the mixing chamber to an ice maker where it is made into ice. The solution in ice form initially contains less than three parts (and preferably less than one part) per million of free chlorine dioxide. The ice is then delivered to the environment where chlorine dioxide ($ClO_2$) is desired. In that environment, there is a slow release of chlorine dioxide ($ClO_2$) gas from the ice. The ice is preferably put into contact with a food item so that the food item will be cooled by the ice as it melts and will be contacted by the chlorine dioxide ($ClO_2$) as it is produced.

The homogenous, acidified sodium chlorite solution may be removed from the mixing chamber as a liquid and introduced into water and be used for water treatment. Or, it can be used for food plant sanitation. Also, it can be used as an antimicrobial solution for direct treatment of food items.

Another aspect of the invention is to provide an apparatus for producing a homogeneous, acidified sodium chlorite and water solution. The apparatus is basically characterized by a mixing chamber having an inlet and an outlet, a conduit having an inlet end connected to receive water under pressure, and an outlet end connected to the inlet of the mixing chamber. The apparatus also includes a source of sodium chlorite ($NaClO_2$), a first feed line leading from said source of sodium chlorite ($NaClO_2$) to the conduit, and a first feed pump in the first feed line. The apparatus further includes a source of acid solution. A second feed line leads from the source of acid solution to the conduit. It makes a connection with the conduit between the first feed line to the conduit and the inlet of the mixing chamber. A second feed pump is in the second feed line. In use, water under pressure is delivered into the inlet of the conduit. The first feed pump is used to pump sodium chlorite ($NaClO_2$) into the conduit, in admixture with the water in the conduit. The second feed pump is used to feed the acid solution into the conduit in admixture with the sodium chlorite ($NaClO_2$) and water. The sodium chlorite ($NaClO_2$), water and acid solution is then delivered into the mixing chamber and in the mixing chamber where it is mixed to homogenize the solutions.

In preferred form, at least one flow meter is provided in the conduit upstream of the first feed line. The flow meter produces a control signal. The control signal is used to control the first feed pump and may also be used to control the second feed pump. Or, the system may include a second flow meter in the conduit upstream of the first feed line. In such case, the first flow meter produces a control signal that is used to control the first feed pump. The second flow meter produces a control signal that is used to control the second feed pump.

According to an aspect of the invention, the conduit is divided into two branches which extend for a while as two flow paths. Then, the two branches come back together and join a single part of the conduit that leads into the inlet of the mixing chamber. In such system, the sodium chlorite ($NaClO_2$) is pumped by the first feed pump into the first branch. The acid solution is pumped by the second feed pump into the second branch. The second branch delivers the acid solution into admixture with the sodium chlorite ($NaClO_2$)

solution that is flowing in the first branch. The admixture occurs where the first and second branches come back together and join the conduit section that leads into the inlet of the mixing chamber.

These and other advantages and features will become apparent from the detailed description of the best mode for carrying out the invention.

BRIEF DESCRIPTION OF THE DRAWINGS

In the drawings, like element designations refer to like parts throughout the several views, and:

FIG. 3 is a more complete schematic diagram of the system that is shown in FIG. 1;

FIG. 4 is a view like FIG. 3 but showing a modified system in which the conduit that leads from the water intake to the inlet of the mixing chamber is divided into two branches, the sodium chlorite ($ClO_2$) solution is fed into the water in the first branch, the acid solution is delivered into the water in the second branch, and the branches are combined into a single conduit section that leads into the inlet of the mixing chamber;

DETAILED DESCRIPTION OF THE INVENTION

Figure 1:
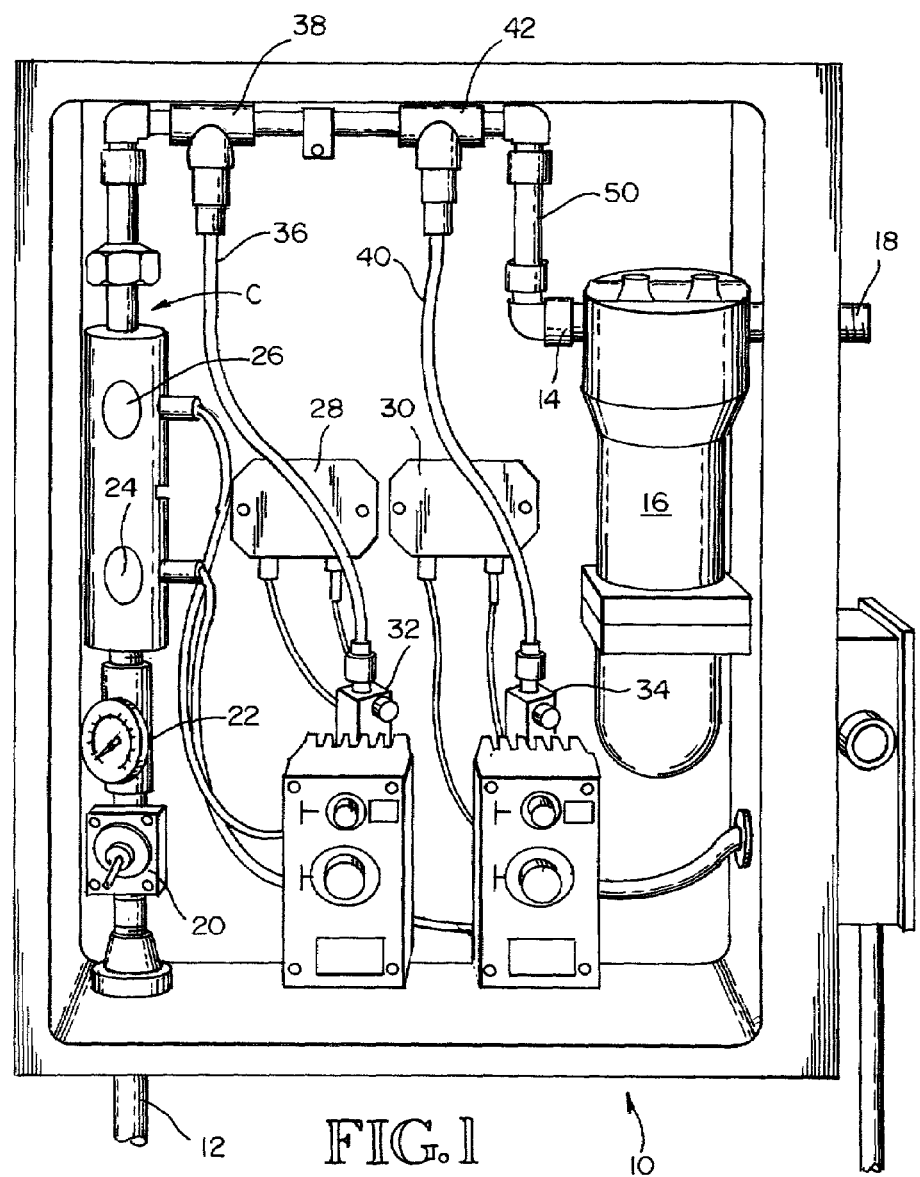
FIG. 1 is a pictorial view looking into a cabinet that contains the preferred apparatus for producing an acidified sodium chlorite and water solution.

FIG. 1 shows a system of the present invention housed within a cabinet 10. A conduit 12 delivers a water stream into a conduit C inside the cabinet 10 that extends from the conduit 12 to the inlet 14 leading into a mixing chamber 16. Mixing chamber 16 includes an outlet conduit 18 that extends outwardly through an opening in a sidewall of the cabinet 10. Inside the cabinet 10, the conduit C includes a pressure regulator 20 and a standard pressure gauge 22. Flow measuring paddle wheels 24, 26, or any other suitable flow measuring device, are used to generate and send electrical signals, at a frequency proportional to the flow of water through them, to pulse dividers 28, 30. These adjustable pulse dividers render the number of pulses per minute (or per gallon of water) down to a frequency acceptable to chemical feed pumps 32, 34. Feed pump 32 is connected to pump a dilute solution of sodium chlorite ($NaClO_2$). Pump 34 pumps a mild mineral or organic acid or acid preparation. The acid solutions are preferably phosphoric acid, citric acid, and any preparations of them containing other ingredients such as detergents, chelating agents, or other agitives.

The dilute solution of sodium chlorite ($NaClO_2$) is delivered by a first feed line 36 into a region 38 of the conduit C in the cabinet 10. The mild mineral or organic acid or acid preparation is delivered by a feed line 40 into a second region 42 in the conduit that is downstream of region 38. The reactants are fed separately into the water stream within the conduit so as to deliberately avoid mixing the relatively concentrated precursor chemicals. Finally, the water stream containing the reactants are fed into the inlet 14 of the mixing chamber 16 which acts to smooth out the pulsating delivery by the chemical feed pumps 28, 30.

Figure 2:
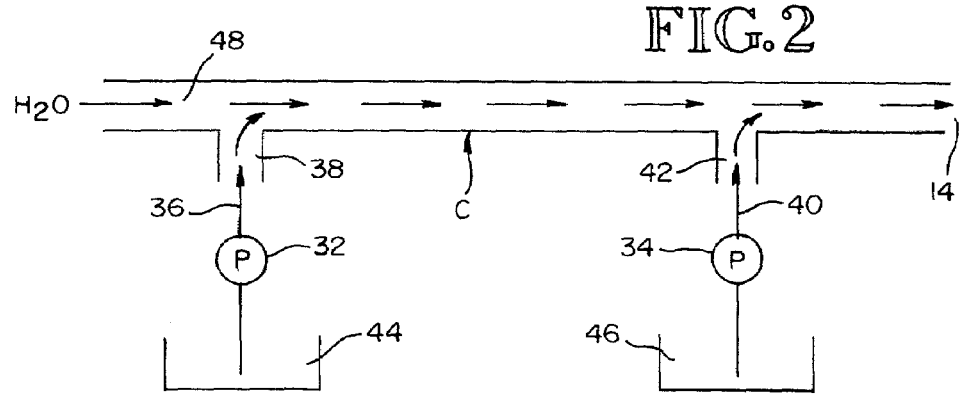
FIG. 2 is a very basic schematic diagram of the system shown by FIG. 1.

FIG. 2 shows a source of sodium chlorite ($NaClO_2$) solution 44 and a source of an acid solution 46. The sodium chlorite ($NaClO_2$) solution 44 is delivered at location 38 in conduit C into admixture with water 48 that is delivered to conduit C by conduit 12. There is some mixing of the sodium chlorite ($NaClO_2$) solution 44 with the water 48 before the combined solutions reach region 42 of conduit C. At region 42, the feed line 40 delivers a water and acid solution 46 into the flowing water and sodium chlorite ($NaClO_2$) solution that is flowing through the conduit C. The water and acid solution mixes with the water and chlorite ($NaClO_2$) solution where they flow together in section 50 of conduit C and within the mixing chamber 16.

By way of typical and therefore nonlimitive example, the components shown in FIG. 1 may be as follows. The water pressure regulator 20 may be a ¾" N35B U, EDP#0006808, 25–75 psi., Watts Regulator Co., North Andover, Mass. 01845. The pressure gauge 22 may be a 2 inch dial, ⅛" thread, 0–60 psi, BCG Gauges or "over the counter" equivalent. The flow meters 24, 26 may be paddle wheels, Seametrics Model SPX-075225, Seametrics, Inc. 20419 80$^{th}$ Ave. S., Kent, Wash. 98032. The pulse dividers 28, 30 may be Seametrics Model PD-10W, Seametrics, Inc. 20419 80$^{th}$ Ave. S., Kent, Wash. 98032. The chemical feed pumps 32, 34 may be LMI Milton Roy Model A751-392SI, LMI Milton Roy Co. 8 Post Office Square, Acton, Mass. 01720. The mixing chamber 16 may be a AMATEK Filter Housing, #10, Clear USFilter, 181 Thornhill Rd., Warrendale, Pa. 15086.

FIG. 3 is a more complete schematic diagram of the system shown by FIG. 1. The particular mixing chamber 16 that is illustrated has the inlet 14 and the outlet 18 near its top. However, the inlet 14 feeds downwardly into a center tube that is open at its lower end. The solution flows out of the center tube into an annular chamber that surrounds the center tube and flows back upwardly in the annular chamber to the outlet 18. This is but one of a number of types of mixing chambers that can be used.

FIG. 4 shows a modified system. It is like the system shown by FIG. 3 except that the conduit C divides into two branches C1, C2 and then combines back into a single conduit section 50 that connects to the mixing chamber inlet 14. In this embodiment, feed pipe 36 delivers the sodium chlorite ($NaClO_2$) solution to water in a branch (or flow path) C1. The feed pipe 40 delivers the acid solution into a conduit branch (or flow path) C2, into admixture with water in that branch C2. The water and acid solution is then admixed at 52 into the water and sodium chlorite ($NaClO_2$) solution leaving branch C1 and entering into conduit section 50. In this embodiment, the sodium chlorite ($NaClO_2$) and the acid are both diluted a considerable amount by water before they are brought into contact with each other in the conduit section 50.

In preferred form, a very small amount of $NaClO_2$ is added to a very large amount of water and a very small amount of the acid solution is added to a very large amount of water. After being united, the two dilute streams are mixed in the mixing chamber 16 and the combined solution is later utilized in one of several manners, as will be described below. This manner of combining the constituents slows the formation of chlorine dioxide ($ClO_2$). The system of the invention generally does not use strong mineral acids such as hydrochloric acid because when such a strong mineral acid is used it will form chlorine dioxide too swiftly for time-release applications. The constituents are slow to act to form the chlorine dioxide gas ($ClO_2$) and there is a slow release of the chlorine dioxide gas ($ClO_2$). There is a time release.

Care is taken to produce a strong enough solution to produce sufficient chlorine dioxide ($ClO_2$) to eliminate spoilage and pathogenic organisms on food items, but at the same time weak enough to prevent any oxidation of the food items, and weak enough to obtain the desired slow, time release of the chlorine dioxide gas ($ClO_2$).

Figure 5:
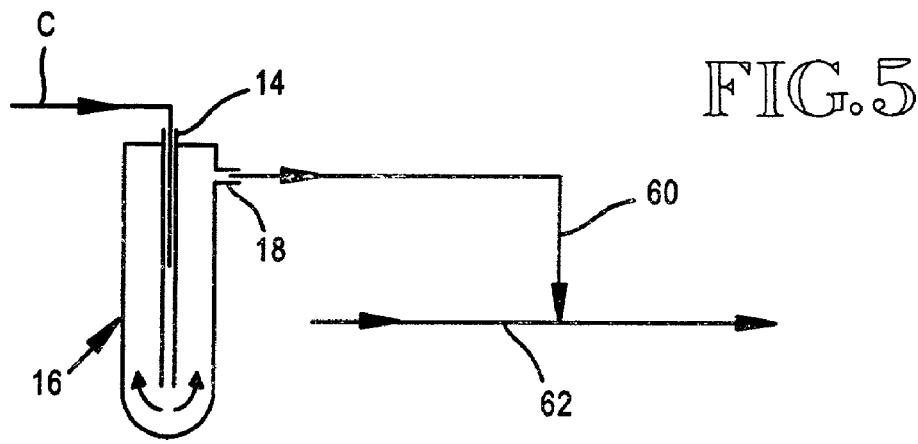
FIG. 5 is a schematic diagram showing the effluent of the mixing chamber being fed into a conduit into admixture with a liquid in the conduit.

The solutions that are delivered into the mixing chamber 16 are substantially thoroughly mixed in the mixing chamber. The effluent of the mixing chamber 16 is a substantially homogenous, acidified sodium chlorite solution. This solution will slowly produce and release chlorine dioxide gas ($ClO_2$) over a period of hours and even days. FIG. 5 shows the substantially homogenous, acidified sodium chlorite solution being delivered by conduit 60 into admixture with water in a conduit 62. As the sodium chlorite gas ($ClO_2$) is released in the water, it will purify the water.

Figure 6:
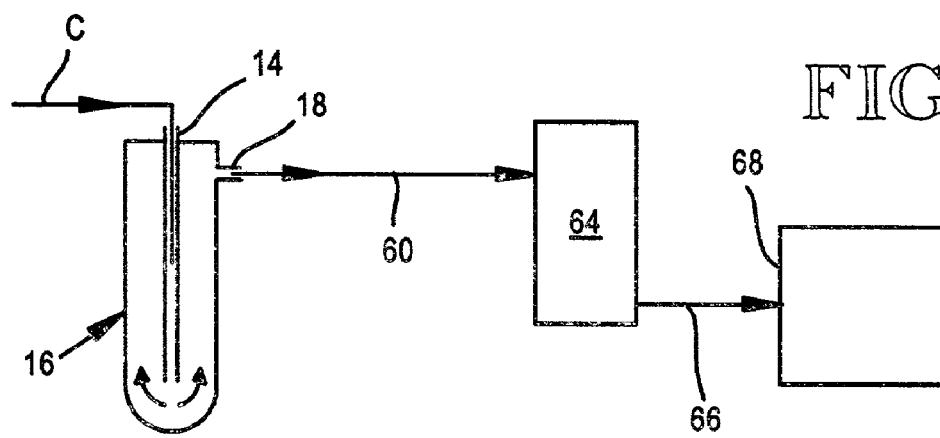
FIG. 6 is a view like FIG. 5 but showing the effluent from the mixing chamber being fed into an ice maker and the ice maker delivering ice to a container of a food item that will receive the ice.

FIG. 6 shows the effluent from the mixing chamber 16 being delivered into an ice maker 74. Ice 66 that is discharged from the ice maker 64 (e.g. as flake ice) contains the acidified sodium chlorite. When the acidified sodium chlorite solution is frozen, the release of chlorine dioxide gas ($ClO_2$) is slowed substantially and will usually occur over a period of days. When the acidified sodium chlorite solution is not frozen, the chlorine dioxide gas ($ClO_2$) will be released over a period of hours, or at least fastener than it is released from ice. FIG. 6 shows the ice 62 being delivered into a vessel 68 that may contain a food item, such as meat, fish, or a vegetable. The ice keeps the food item cold and when the chlorine dioxide gas ($ClO_2$) is released, it contacts and treats the food item.

Figure 7:
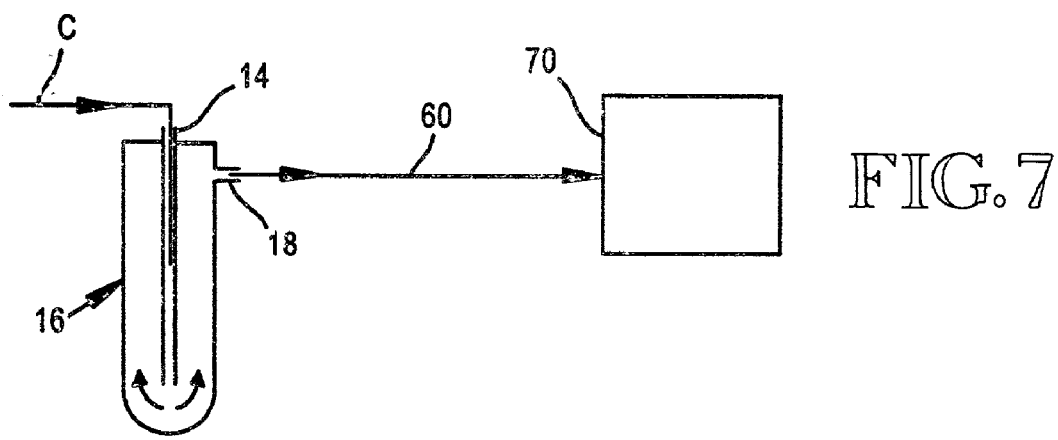
FIG. 7 is a view like FIGS. 5 and 6 but showing the effluent from the mixing chamber being delivered into a container that contains a food item or some other item to be treated by the chlorine dioxide ($ClO_2$) that evolves from the homogeneous, acidified sodium chlorite solution.

FIG. 7 shows the effluent 60 from the mixing chamber being introduced into or onto a space 70, into contact with a food item, to serve as an antimicrobial solution for direct treatment of the food item. The region 70 may be a container or a region on a conveyor used for conveying the food item. In this installation, the effluent can be sprayed onto the food item, such as disclosed in the aforementioned U.S. Pat. No. 5,863,584, for example.

While specific embodiments of the present invention have been shown and described in detail to illustrate the utilization of the inventive principles, it is to be understood that such showing and description have been offered by way of example, and not by way of strict limitation. Protection by Letters Patent of this invention and all of its aspects are set forth in the appended claims and is sought to the broadest extent that the prior art allows.

What is claimed is:

1. A method of producing an acidified sodium chlorite and water solution capable of releasing clorine dioxide, comprising:
   forming a flowing water and acid solution by admixing an about one part flowing acid solution into an about one thousand eight hundred (1,800) parts flowing water stream,
   admixing the flowing water and acid solution into a flowing water and sodium chlorite ($NaClO_2$) solution;
   flowing the combined solutions into and through a mixing chamber to form a homogenous, acidified sodium chlorite solution in the mixing chamber; and
   removing the homogenous, acidified sodium chlorite solution from the mixing chamber.

2. A method of producing an acidified sodium chlorite and water solution capable of releasing chlorine dioxide, comprising:
   admixing a flowing water and acid solution into a flowing water and sodium chlorite ($NaClO_2$) solution comprising about one part sodium chlorite ($NaClO_2$) solution to about one thousand eight hundred (1,800) parts of water;
   flowing the combined solutions into and through a mixing chamber to form a homogenous, acidified sodium chlorite solution in the mixing chamber; and
   removing the homogenous, acidified sodium chlorite solution from the mixing chamber.

3. A method of producing chlorine dioxide over a period of time, comprising:
   forming a flowing water and acid solution by admixing a flowing acid solution into a flowing water stream at a ratio of about one part acid solution to about one thousand eight hundred (1,800) parts of water;
   admixing the flowing water and acid solution into a flowing water and sodium chlorite ($NaClO_2$) solution;
   flowing the combined solutions into and through a mixing chamber to form a homogenous, acidified sodium chlorite solution in the mixing chamber; and
   removing the homogenous, acidified sodium chlorite solution from the mixing chamber and delivering it to an environment in which chlorine dioxide ($ClO_2$) is desired, whereby in such environment the chlorine dioxide ($ClO_2$) will be slowly produced by and released from the homogenous, acidified sodium chlorite solution, over a period of time.

4. A method of producing chlorine dioxide over a period of time, comprising:
   forming a flowing water and sodium chlorite ($NaClO_2$) solution by admixing about one part sodium chlorite ($NaClO_2$) solution to about one thousand eight hundred (1,800) parts of water;
   admixing a flowing water and acid solution into the flowing water and sodium chlorite ($NaClO_2$) solution;
   flowing the combined solutions into and through a mixing chamber to form a homogenous, acidified sodium chlorite solution in the mixing chamber; and
   removing the homogenous, acidified sodium chlorite solution from the mixing chamber and delivering it to an environment in which chlorine dioxide ($ClO_2$) is desired, whereby in such environment the chlorine dioxide ($ClO_2$) will be slowly produced by and released from the homogenous, acidified sodium chlorite solution, over a period of time.

5. A method of producing chlorine dioxide over a period of time, comprising:
   forming a flowing water and acid solution by admixing a flowing acid solution into a flowing water stream at a ratio of about one part acid solution to about one thousand eight hundred (1,800) parts of water;
   admixing the flowing water and acid solution into a flowing water and sodium chlorite ($NaClO_2$) solution;
   flowing the combined solutions into and through a mixing chamber to form a homogenous, acidified sodium chlorite solution in the mixing chamber; removing the homogenous, acidified sodium chlorite solution from the mixing chamber and delivering it to an environment in which chlorine dioxide ($ClO_2$) is desired, whereby in such environment the chlorine dioxide ($ClO_2$) will be slowly produced by and released from the homogenous, acidified sodium chlorite solution, over a period of time; and comprising delivering the homogenous, acidified sodium chlorite solution to an ice maker, freezing it in the ice maker to make ice in which the free chlorine dioxide content is initially less than three parts per million, and then delivering the ice to the environment where chlorine dioxide ($ClO_2$) is desired, whereby there is a slow release of chlorine dioxide ($ClO_2$) gas from the ice as the ice melts.

6. A method of producing chlorine dioxide over a period of time, comprising:

admixing about one part sodium chlorite ($NaClO_2$) solution to about one thousand eight hundred (1,800) parts of water to form a flowing water and sodium chlorite ($NaClO_2$) solution;

admixing a flowing water and acid solution into the flowing water and sodium chlorite ($NaClO_2$) solution;

flowing the combined solutions into and through a mixing chamber to form a homogenous, acidified sodium chlorite solution in the mixing chamber;

removing the homogenous, acidified sodium chlorite solution from the mixing chamber and delivering it to an environment in which chlorine dioxide ($ClO_2$) is desired, whereby in such environment the chlorine dioxide ($ClO_2$) will be slowly produced by and released from the homogenous, acidified sodium chlorite solution, over a period of hours to days; and delivering the homogenous, acidified sodium chlorite solution to an ice maker, freezing it in the ice maker to make ice in which the free chlorine dioxide content is initially less than three parts per million, and then delivering the ice to the environment where chlorine dioxide ($ClO_2$) is desired, whereby there is a slow release of chlorine dioxide ($ClO_2$) gas from the ice as the ice melts.

7. The method of claim 1, comprising admixing about one part sodium chlorite ($NaClO_2$) solution to about one thousand eight hundred (1,800) parts of water.

8. The method of claim 2, comprising forming the flowing water and acid solution by admixing a flowing acid solution into a flowing water stream.

9. The method of claim 3, comprising admixing about one part sodium chlorite ($NaClO_2$) solution to about one thousand eight hundred (1,800) parts of water.

10. The method of claim 4, comprising forming the flowing water and acid solution by admixing a flowing acid solution into a flowing water stream.

11. The method of claim 5, comprising admixing about one part sodium chlorite ($NaClO_2$) solution to about one thousand eight hundred (1,800) parts of water.

12. The method of claim 6, comprising forming the flowing water and acid solution by admixing a flowing acid solution into a flowing water stream.

13. The method of claim 6, comprising putting the ice into contact with a food product, so that the food product will be cooled by the ice and will be contacted by the chlorine dioxide ($ClO_2$) as it is produced.

14. The method of claim 11, comprising putting the ice into contact with a food product, so that the food product will be cooled by the ice and will be contacted by the chlorine dioxide ($ClO_2$) as it is produced.

15. The method of claim 12, comprising putting the ice into contact with a food product, so that the food product will be cooled by the ice and will be contacted by the chlorine dioxide ($ClO_2$) as it is produced.

16. The method of claim 3, wherein the environment is a food plant environment, whereby in such environment the chlorine dioxide ($ClO_2$) will be slowly produced and released from the homogenous, acidified sodium chlorite solution over a period of time and will sanitize the food plant.

17. The method of claim 3, wherein the environment includes food items that are positioned to be contacted by the chlorine dioxide ($ClO_2$) as it is produced, whereby the chlorine dioxide ($ClO_2$) will act as an antimicrobial solution for direct treatment of the food item.

\* \* \* \* \*